United States Patent
Jiang et al.

(10) Patent No.: US 11,280,788 B2
(45) Date of Patent: Mar. 22, 2022

(54) RAPID DIAGNOSIS OF PERITONITIS IN PERITONEAL DIALYSIS PATIENTS

(71) Applicant: Fresenius Medical Care Holdings, Inc., Waltham, MA (US)

(72) Inventors: Tao Jiang, Knoxville, TN (US); Changna Wang, Farmington, UT (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 0 days.

(21) Appl. No.: 16/752,518

(22) Filed: Jan. 24, 2020

(65) Prior Publication Data
US 2020/0249228 A1 Aug. 6, 2020

Related U.S. Application Data

(60) Provisional application No. 62/799,430, filed on Jan. 31, 2019.

(51) Int. Cl.
*G01N 33/569* (2006.01)

(52) U.S. Cl.
CPC ... *G01N 33/56911* (2013.01); *G01N 2469/10* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 5,602,040 A | 2/1997 | May et al. | |
| 6,485,982 B1 | 11/2002 | Charlton | |
| 6,924,153 B1 | 8/2005 | Boehringer et al. | |
| 7,785,899 B2 | 8/2010 | Saul et al. | |
| 7,893,219 B2 | 2/2011 | Casson et al. | |
| 8,128,871 B2 | 3/2012 | Petruno et al. | |
| 8,962,260 B2 * | 2/2015 | Sambursky | G01N 33/523 435/7.1 |
| 2005/0191717 A1 * | 9/2005 | Martis | C12Q 1/04 435/14 |
| 2005/0250141 A1 | 11/2005 | Lambert et al. | |
| 2011/0020323 A1 | 1/2011 | Beaumont et al. | |
| 2014/0242613 A1 | 8/2014 | Takeuchi et al. | |
| 2015/0241424 A1 * | 8/2015 | Lawrence | G01N 33/585 506/9 |
| 2016/0327580 A1 | 11/2016 | Burger-Kentischer et al. | |
| 2018/0356413 A1 | 12/2018 | Parekh | |

FOREIGN PATENT DOCUMENTS

| | | | |
|---|---|---|---|
| WO | 2009/063307 A2 | 5/2009 | |
| WO | 2018/007013 A2 | 1/2018 | |
| WO | 2018/060708 A1 | 4/2018 | |
| WO | WO-2018060708 A1 * | 4/2018 | ............... C12Q 1/02 |

OTHER PUBLICATIONS

Ostrosky-Zeichner et al. 2005 (Multicenter Clinical Evaluation of the (1-3) b-d-Glucan Assay as an Aid to Diagnosis of Fungal Infections in Humans; CID 2005:41, pp. 654-659). (Year: 2005).*
Lin et al. 2013 (Pathogen-Specific Local Immune Fingerprints Diagnose Bacterial Infection in Peritoneal Dialysis Patients; J. Am. Soc. Nephrol. 24:2002-2009, 2013). (Year: 2013).*
Lippi et al. 2013 (Assessment of neutrophil gelatinase-associated lipocalin and lactate dehydrogenase in peritoneal fluids for the screening of bacterial peritonitis; Clinica Chima Acta; 418: 59-62). (Year: 2013).*
International Search Report for International Application No. PCT/US20/15477, dated Jun. 19, 2020, 4 pages.
International Written Opinion for International Application No. PCT/US20/15477, dated Jun. 19, 2020, 7 pages.
Ma et al., "Diagnostic and Prognostic Significance of Procalcitonin and Endotoxin in Peritoneal Dialysis-Related Peritonitis", Int. J. Clin. Exp. Pathol., vol. 10, No. 5 (2007), pp. 5984-5988.
Moral et al., "MUL+DO: A Multicomponent Index for the Quick Diagnosis of Peritonitis in Peritoneal Dialysis Patients," Nefrologia, vol. 38, No. 3, (2018), pp. 273-278.
Ranco et al., "Peritoneal Dialysis: A Clinical Update," Contrib. Nephrol. Basel, Karger, vol. 150, (2006), pp. 187-194.

* cited by examiner

Primary Examiner — Mary Maille Lyons
(74) Attorney, Agent, or Firm — TraskBritt

(57) ABSTRACT

Described is an assay for diagnosing an infection such as peritonitis in a subject. The assay includes a binding molecule, such as an antibody that specifically binds to an inflammatory marker in a sample from the subject, and a second binding molecule that binds to a marker indicative of a pathogen in the sample. For diagnosing peritonitis in a subject, the pathogen will be at least one bacterium and/or fungus. Typically, the assay will be incorporated into a lateral flow device and may include a binding molecule that specifically binds to an antigen indicative of the presence of a specific pathogen species. The described assay(s) may further include filter(s), enriching antigen(s), and buffer(s). Also described are methods of diagnosing and treating peritonitis in a subject who is a peritoneal dialysis patient that include utilizing the herein described assay(s) or assay kit(s) to analyze the subject's peritoneal dialysis effluent.

16 Claims, 7 Drawing Sheets

RAPID DIAGNOSIS OF PERITONITIS IN PERITONEAL DIALYSIS PATIENTS

CROSS-REFERENCE TO RELATED APPLICATION

The application claims the benefit under 35 U.S.C. § 119(e) of U.S. Provisional Patent Application No. 62/799,430 filed on Jan. 31, 2019, the contents of which are incorporated herein by this reference.

TECHNICAL FIELD

The application relates generally to medical devices, and more particularly to a diagnostic system, apparatus, and associated methods useful for, among other things, diagnosing and treating a peritoneal dialysis patient for peritonitis.

BACKGROUND

Peritonitis is a major cause of morbidity and mortality in peritoneal dialysis ("PD") patients globally. According to the International Society for Peritoneal Dialysis ("ISPD") guidelines, peritonitis can be diagnosed when at least two of the following are present: (1) clinical features consistent with peritonitis, e.g., abdominal pain and/or cloudy dialysis effluent ("CDE"); (2) dialysis effluent with a white blood cell count ("WBC") greater than 100/µL or greater than $0.1 \times 10^9$/L (after a dwell time of at least two hours), with more than 50% of the WBCs being polymorphonuclear ("PMN"); and (3) a positive peritoneal dialysis effluent ("PDE") culture.

However, in practice, when a patient presents in the clinic with symptoms of peritonitis, it typically takes clinicians from a couple of hours to five days to get the results of a white blood cell count and peritoneal dialysis effluent cell culture. There is also about a 10% culture-negative rate even with infections. A fast, reliable way to confirm infection is needed to prevent patient deterioration due to delay in treatment.

Once an infection diagnosis is made (without knowing the specific causative agent(s)), the nephrologist typically initiates empirical antibiotic therapy immediately. Such therapy typically includes administering at least two different broad spectrum antibiotics which collectively cover most of the gram-positive and gram-negative bacteria, along with an anti-fungal agent to prevent secondary fungal peritonitis until the causative agent(s) and drug susceptibility tests become available.

The long-term use of broad spectrum antibiotics is however known to be associated with the risk of developing drug-resistant bacteria and an increased risk of subsequent fungal infection. Therefore, an early, rapid and culture-independent method is needed to identify the causative agent(s) of infection, support the prescription of suitable antibiotics, and reduce some of these unintended complications.

At present, a simple device is not available for at-home peritoneal dialysis patients or for clinicians in dialysis clinics to confirm the presence of infection as well as to identify the putative causative agents or class of causative agents.

A product from Mologic Ltd. (UK) detects certain inflammatory markers, such as IL-6 and MMP8, in peritoneal dialysis effluent to alert peritoneal dialysis patients of inflammation and encourage further investigation. However, the product does not specifically identify the causative agent(s) of infection, which would assist in, e.g., prescribing antibiotics. Furthermore, inflammation may be present in some cases where there is no infection, such as inflammation caused by chemical irritants, mechanical injury to the peritoneum, or other conditions. In such cases, inflammatory status alone does not provide sufficient information for a clinician to make a timely and specific decision about treatment.

WO2018/060708 describes a method of chemically detecting leukocytes (e.g., using redox indicators), and optionally simultaneously discriminating between gram-positive and gram-negative bacteria in peritoneal dialysis effluent. However, the described method is not specific for causative agent(s) of infection, and requires incubation times of at least two hours, and more typically 12 hours or more. Another limitation of the method is that it may not distinguish between Gram negative infections and infection with both Gram positive and Gram negative bacteria.

Other devices may be useful to determine gram status of bacteria in bodily fluids, but they cannot simultaneously detect inflammation, and/or they cannot indicate specific bacterial species known that may be associated with peritonitis.

A turbidity check of peritoneal dialysis effluent is another technology used by the Renal Research Institute ("RRI") and liberDi. Ronco C, Dell'Aquila R, Rodighiero MP (eds): "Peritoneal Dialysis: A Clinical Update," *Contrib. Nephrol.*, Basel, Karger, 2006, vol. 150, pp 187-194. The principle is to predict peritonitis by evaluating the WBC count based upon turbidity. However, there are many reasons other than just high levels of WBCs that can change the turbidity level in peritoneal dialysis effluent. Furthermore, the sensitivity of a turbidity-based WBC test may be inadequate for use with many continuous ambulatory peritoneal dialysis ("CAPD") patients.

Yet another technology from DxNow is a portable bioimaging system with microfluidic-based consumables for prediction of peritonitis. The principle is to capture WBCs in peritoneal dialysis effluent using WBC-specific antibodies and then conducting a count. This technology is intended to provide an accurate WBC count in a short time, however, it does not provide any information regarding causative agents and the device is sophisticated and relatively expensive.

Other platforms are based on PCR or other nucleic acid-based amplification/detection methodology. While these may be sensitive, they typically require bulky and expensive equipment, specialized training, and relatively long incubation periods (2+ hours), so may not be practical in many point-of-care applications where a determination is desired in minutes or less than an hour, particularly for use in the home or remote clinic setting Accordingly, despite a long-term need for rapid, early detection of inflammation and specific Gram/microbial status of peritonitis in PD patients, no suitable solution has yet been identified.

The described system can be used to perform, from the perspective of the user, a single test with easy sample pre-treatment.

BRIEF SUMMARY

Described is an assay for diagnosing an infection in a subject, which assay includes a first binding molecule that specifically binds an inflammatory marker in a sample taken from the subject, and a second binding molecule that binds a marker indicative of the presence of a pathogen in the sample. The first binding molecule and the second binding molecule may be present on one test device or test strip.

Also described is an assay kit that includes a binding molecule that specifically binds an antigen indicative of an inflammatory response in the peritoneum; a binding molecule that specifically binds an antigen indicative of the presence of gram-positive bacteria; and a binding molecule that specifically binds an antigen indicative of the presence of gram-negative bacteria. Such an assay kit may further include a binding molecule that specifically binds an antigen indicative of the presence of a fungus. The assay kit may further include a secondary binding molecule or molecules capable of binding to the indicated binding molecules. The secondary binding molecules may be conjugated to a reporter or indicator, such as a fluorescent reporter or other colorable reporter, nanoparticle, reactive particle such as an enzyme, or other reporter or indicator. The binding molecules and secondary binding molecules may be, for example, antibodies.

Typically, the antigen indicative of an inflammatory response in the peritoneum is neutrophil gelatinase-associated lipocalin ("NGAL"), interleukin 1 ("IL-1"), interleukin 6 ("IL-6"), interleukin 8 ("IL-8"), tumor necrosis factor α ("TNFα"), procalcitonin, and/or C-reactive protein ("CRP"). Lipoteichoic acid ("LTA") is an antigen indicative of the presence of gram-positive bacteria. Lipopolysaccharide ("LPS") is an antigen indicative of the presence of gram-negative bacteria. β-glucan is an antigen indicative of the presence of a fungus.

For diagnosing peritonitis in a subject, the pathogen will typically be at least one bacterium and/or fungus.

In certain embodiments, the assay/assay kit will include a binding molecule that specifically binds an antigen indicative of the presence of a specific pathogen species. For use with a peritoneal dialysis effluent, the specific pathogen will typically be *Staphylococcus aureus, Pseudomonas* sp., *Staphylococcus epidermidis, Staphylococcus haemolyticus, Candida* sp., *Escherichia coli*, vancomycin-resistant enterococci, and combinations thereof.

Typically, the assay will be incorporated into a lateral flow device, which will produce results almost instantly, e.g., on the order of minutes. In general, a lateral flow device comprises one or more panels to detect one or more antigens.

In one embodiment, multiple lateral flow devices can be integrated together to detect multiple antigens. Each lateral flow device comprising one or more panels may share a single sample reservoir.

In another embodiment, multiple lateral flow devices can be kept in the same housing but separated to detect antigens by use of individual panels.

In another embodiment, a single lateral flow device can be built in a multiplex format to detect multiple antigens using a single panel.

The described assay(s)/assay kit(s) may further include means for filtering (e.g., a filter), concentrating (e.g., centrifugation), lysing cells, and/or enriching antigen(s) from the PDE.

Sensitivity may be enhanced by concentrating the PDE, particularly for gram-positive and gram-negative antigens/markers. In certain embodiments, a syringe is used to filter and concentrate the PDE rather than a centrifuge.

The described assay(s)/assay kit(s) may further include a buffer that specifically elutes antigen(s) from the assay kit. The buffer composition may be chosen to selectively stabilize the antigen and/or antigen-antibody complex, maintain pH, maintain or disrupt structure or binding of the antigen-antibody complex.

Further described are methods of diagnosing peritonitis in a subject who is a peritoneal dialysis patient that include utilizing the herein described assay(s) or assay kit(s) to analyze the subject's peritoneal dialysis effluent.

In certain embodiments, a method of diagnosing peritonitis in a subject who is a peritoneal dialysis patient includes detecting in a peritoneal dialysis effluent ("PDE") from the subject an antigen indicative of an inflammatory response having been launched in the peritoneum; detecting (e.g., utilizing appropriate binding molecule(s)) in the PDE an antigen indicative of the presence of gram-positive bacteria; and detecting (e.g., utilizing appropriate binding molecule(s)) in the PDE an antigen indicative of the presence of gram-negative bacteria. Preferably, results are provided in less than an hour.

In certain embodiments, the method further includes detecting (e.g., by utilizing appropriate binding molecule(s)) in the peritoneal dialysis effluent an antigen indicative of the presence of a fungus.

In certain embodiments, the method further includes filtering, concentrating, and/or enriching the peritoneal dialysis effluent prior to detecting antigen(s). In certain embodiments, enrichment may be by, for example, placing 50 ml of PDE into a conical tube, followed by centrifugation of the PDE sample, and treatment with, e.g., a lysis buffer, extraction buffer, and neutralization buffer. Enrichment of a PDE sample for antigens may also be by use of an ultrafiltration ("UF") membrane (e.g., molecular weight cutoff 29,000). In another embodiment, a syringe is used to pass/push the PDE through a UF membrane instead of a centrifuge.

Such diagnostic methods can be used to treat peritonitis in the subject by first diagnosing the subject as having peritonitis and then administering an appropriate antibiotic to the subject to treat the peritonitis in view of the diagnosis.

In a particularly preferred embodiment, a paper device that utilizes lateral flow assay technology and/or dry chemistry test technology is disclosed to simultaneously detect the presence of cell wall components and/or surface antigen(s) from contaminating microorganisms and/or inflammatory biomarkers in a patient's PDE. In some embodiments, lateral flow technology and/or dry chemistry test technology is used to rapidly assist clinicians in diagnosing an infection in the peritoneal dialysis patient when the patient presents in the clinic with cloudy peritoneal dialysis effluent and/or other symptoms of peritonitis. In certain embodiments, detection is based upon a lateral flow test (also known as a lateral flow immunochromatographic assay), which is a simple, paper-based device used to detect the presence of a target analyte in a liquid sample without the need for specialized and costly equipment. The device aids in the determination of the contaminating microorganism(s) so that, for example, appropriate antibiotics therapy can be promptly prescribed.

The device and associated methods for using it assist clinicians (and patients and caregivers) in quickly determining the existence of an infection in a peritoneal dialysis patient and aid in providing treatment therefore so as to improve the management of peritoneal dialysis-related peritonitis. A goal is to thus rapidly and simultaneously detect the presence of multiple molecular markers that are released from the patient's host immune system and/or pathogens as soon as the invasion of pathogens is thought to have occurred in the patient.

DETAILED DESCRIPTION

Figure 1:
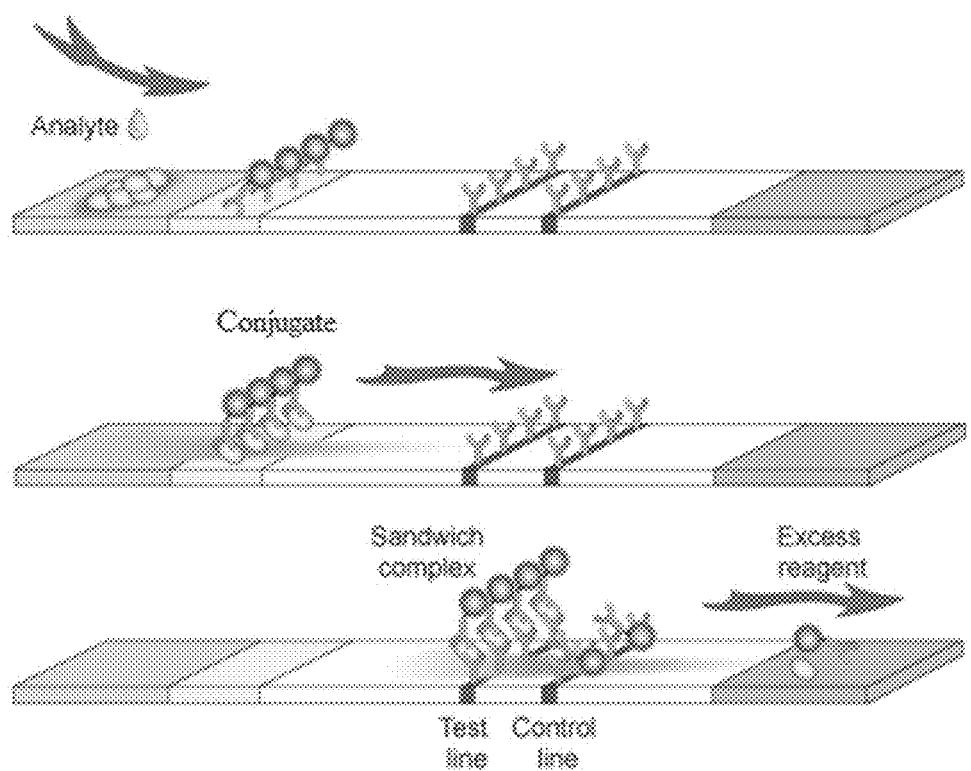
FIGS. 1 through 5 and 7 depict various embodiments of lateral flow devices as described herein.

As used herein, a "binding molecule," e.g., an antibody (monoclonal or polyclonal) or antigen-binding fragment thereof, aptamer, affimer (peptide aptamer), receptor binding domain, or designed ankyrin repeat proteins (DARPins) is a molecule that specifically binds an antigen. The term "antigen-binding fragments" means a portion of an intact binding molecule, such as an antibody. Examples of antibody fragments include Fab, Fab', F(ab')2 and Fv fragments, CDR, antigen-binding site, heavy or light chain variable region, diabodies, triabodies single chain antibody molecules ("scFv") and multi-specific antibodies formed from at least two intact antibodies or fragments thereof or peptides or polypeptides that contain at least a fragment of an immunoglobin that is sufficient to confer antigen binding to the peptide or polypeptide, etc. An antigen-binding fragment may comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the antibody. The antigen-binding fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by: E. Harlow and D, Lane (1988), Cold Spring Harbor Laboratory, Cold Spring Harbor, New York. An antibody or antigen-binding fragment thereof has one or more binding sites. If there is more than one binding site, the binding sites may be identical to one another or they may be different. The term "specifically binding," or "specifically recognize," as used herein, in reference to the interaction of an antibody and its binding partner, e.g. an antigen, means that the interaction is dependent upon the presence of a particular amino acid sequence or structure, e.g. an antigenic determinant or epitope, on the binding partner. In other words, the antibody preferentially binds or recognizes the binding partner even when the binding partner is present in a mixture of other molecules or organisms. The binding may be mediated by covalent or noncovalent interactions or a combination of both. In yet other words, the term "specifically binding" or "specifically recognizes" means that the antibody is specifically immunoreactive with an antigenic determinant or epitope and is not immunoreactive with other antigenic determinants or epitopes. An antibody that specifically or immunospecifically binds to an antigen may bind to other peptides or polypeptides with lower affinity as determined by, e.g., radioimmunoassays ("RIA"), enzyme-linked immunosorbent assays ("ELISA"), BIACORE, or other assays known in the art. Antibodies or fragments thereof that specifically bind to an antigen may be cross-reactive with related antigens, carrying the same epitope. Preferably, antibodies or fragments thereof that specifically bind to an antigen do not cross-react with other antigens.

Analytes/Associated Specific Binding Molecules:

In certain embodiments, the device is configured to detect one, two, or more inflammatory markers such as, e.g., neutrophil gelatinase-associated lipocalin ("NGAL") and interleukin 6 ("IL-6"), as well as one, two, three, or more cell wall components, such as lipoteichoic acid ("LTA"), lipopolysaccharide ("LPS"), and β-glucan in one device.

NGAL (neutrophil gelatinase-associated lipocalin, lipocalin 2, siderocalin, or neutrophil lipocalin) is a 25 kDa glycosylated single chain monomer and member of the lipocalin family of proteins that bind and transport small lipophilic molecules. NGAL is released by activated neutrophils, as well as renal tubule epithelial cells, cardiomyocytes, uterus, prostate, salivary glands, and other tissues, and can be found in both serum and urine. NGAL can form dimers, forming a 45 kDa disulfide-linked homodimer, small amounts of higher oligomers, and a 135 kDa heterodimer with matrix metalloproteinase 9 ("MMP-9," gelatinase B). NGAL is involved in innate immunity. The homodimer form is specifically released by neutrophils that infiltrate into the peritoneum immediately after the invasion of a pathogen, while the monomer and heterodimer are more generally released by tubular cells and the other indicated tissues in response, for example, to acute kidney injury. During the process of peritonitis, the level of NGAL in peritoneal dialysis effluent correlates well with the quantity of neutrophils, and NGAL levels can be used to predict infection even before any clinical symptoms are noticed. With a lateral flow assay, detection of NGAL appears to be of a higher sensitivity than MMP8 in the peritoneal dialysis effluent samples.

Antibodies that specifically bind NGAL are readily commercially available. For example, a goat IgG polyclonal antibody is available under Catalog #PAS-18382 from ThermoFisher Scientific. Anti-NGAL antibody (ab63929, rabbit polyclonal to NGAL), is available from Abcam (Cambridge, Mass., US).

Interleukin 6 is expressed and secreted by mesothelial cells, which serve as the first layer of the host defense system of the peritoneum. Once pathogens invade, the mesothelial cells upregulate expression of IL-6, and a higher level of IL-6 is thus detectable in the peritoneal dialysis effluent. IL-6 levels rapidly increase in the drained PDE before the onset of peritonitis, during peritonitis, and even after peritonitis.

Antibodies that specifically bind IL-6 are readily commercially available. For example, monoclonal antibodies MAB2061-SP, MAB2061-100, and MAB2061-500 (R&D Systems, Inc. Minneapolis, Minn., US) are human IL-6 antibodies that bind human IL-6 in direct ELISAs, but do not cross-react with recombinant IL-6 from mouse, rat, or pig. Anti-IL-6 antibody (ab6672, rabbit polyclonal to IL-6), is available from Abcam (Cambridge, Mass., US).

IL-6 is however commonly detected in peritoneal dialysis patients (even without infection) due to the continuous irritation that may be caused by the peritoneal dialysis fluid. Therefore, the threshold of IL-6 detection limit is preferably adjusted in the device to more reliably indicate the existence of an infection. In this regard, IL-6 may not be the best marker to use, or may be better to use in combination with other inflammatory markers.

In certain embodiments, IL-6 is replaced with a different inflammatory marker, such as procalcitonin or C-reactive protein ("CRP"). Both of these inflammatory markers are useful in the prediction of peritonitis.

Other inflammatory markers include TNFα, fibrinogen, MPO, HAS, fMLP, A1AT, TIMP2, TIMP1, sICAM, MMP 9, HNE, cystatin C, IL-1b, IL-8, calprotectin, RBP4, MMP 8, MMP 2, desmosine, and SPD.

Monoclonal antibodies against TNFα include infliximab (REMICADE™), adalimumab (HUMIRA™), certolizumab pegol (CIMZIA™), and golimumab (SIMPONI™).

Antibodies that specifically bind fibrinogen are readily commercially available. For example, anti-fibrinogen antibody (ab189490, rabbit monoclonal to fibrinogen), is available from abcam (Cambridge, Mass., US). A polyclonal sheep anti-Human Fibrinogen antibody is available under Catalog #AF4786 from R&D Systems. This antibody detects human fibrinogen in direct ELISAs and Western blots.

Antibodies that specifically bind procalcitonin are readily commercially available. For example, anti-procalcitonin antibody (ab166963, sheep polyclonal to procalcitonin), is available from Abcam (Cambridge, Mass., US). A mouse procalcitonin monoclonal antibody (27A3) is available under Catalog #MA1-20887 from ThermoFisher Scientific. MA1-20887 detects procalcitonin in human samples and has been successfully used in ELISA and Western blot procedures. The MA1-20887 immunogen is an internal fragment of purified, full length, native human calcitonin.

Antibodies that specifically bind to C-reactive protein ("CRP") are readily commercially available. For example, anti-C Reactive Protein antibody (ab31156, rabbit polyclonal to human CRP), is available from Abcam (Cambridge, Mass., US). A mouse CRP monoclonal antibody (P4D7) is available under Catalog #MIC0501 from Invitrogen Antibodies/ThermoFisher Scientific.

Thus, increased levels of NGAL and IL-6 in the peritoneal dialysis effluent indicate both the activation of innate immunity and that there is a host defense in the peritoneum, which are initiated at the beginning of peritonitis.

In certain described embodiments, the device could also use only a gram-positive inflammatory marker(s) with an additional technology. For example, in certain embodiments, using turbidity detection technology (e.g., that of RRI) in combination with a binding molecule that binds a marker indicative of the presence of a pathogen could obviate the use of a binding molecule for an inflammatory marker.

Thus, in certain embodiments, described is a method of treating peritonitis in a subject who is a peritoneal dialysis patient, the method comprising: first determining if turbidity is present in a peritoneal dialysis effluent, analyzing the subject's peritoneal dialysis effluent to determine the identity of an infectious microorganism (e.g., Gram (+), Gram (−) and/or fungal infection), and then administering an appropriate antibiotic to the subject to treat the peritonitis in view of the determination of the identity of the microorganism.

In certain embodiments, turbidity detection may be used in combination with a binding molecule that binds a marker indicative of the presence of a pathogen and a binding molecule that binds an inflammatory marker. Such a combination of indicators can provide additional benefits to the patient or clinician, particularly in early diagnosis of infection and early characterization of specific agents of infection.

Peptidoglycan is a key component of the cell wall of bacteria and thus serves as a reliable marker of bacterial infection, distinguishing other causes of inflammation and/ or infection.

Lipoteichoic acid ("LTA") is a glycerol phosphate surface polymer component of the envelope of Gram-positive bacteria. LTA is anchored via its glycolipids to the membrane and carries a polysaccharide chain extending into the peptidoglycan layer of the cell wall. LTA is released spontaneously into the culture medium during growth of gram-positive bacteria. LTA functions as an immune activator with characteristics very similar to lipopolysaccharide (LPS) from Gram-negative bacteria. LTA binds to CD14 and triggers activation predominantly via Toll-like receptor 2. Although LTA is internalized and traffics to the Golgi, cellular activation in response to LTA occurs at the cell surface.

Antibodies that specifically bind to LTA are readily commercially available. For example, a mouse monoclonal antibody is available under Catalog #MA1-40134 from ThermoFisher Scientific. MA1-40134 detects LTA from gram-positive bacterial samples, and has been successfully used in Western blot, ELISA, flow cytometry, immunofluorescence, and immunohistochemistry (frozen) applications. Another mouse monoclonal antibody (IgG3) is available under Catalog #GWB-9E3242 from Genway Biotech, Inc. (San Diego, Calif., US). Other mouse monoclonal LTA antibodies are available, for example, under Catalog #LS-C102921, LS-C102920, LS-C202488, and LS-C757317 from LifeSpan Biosciences, Inc. (Seattle, Wash., US).

LPS is a cell wall component of gram-negative bacteria. Antibodies that specifically bind LPS are readily commercially available. For example, a rabbit polyclonal antibody preparation is available under Product No. PAB526Ge01 from Cloud-Clone Corp. that has the ability to recognize LPS in immunohistochemical staining and western blotting. A lipopolysaccharide (LPS) mouse monoclonal antibody is available under Catalog No. CAU29364 from Biomatik (Cambridge, Ontario, Calif.).

β-glucan is a cell wall component of fungi. Antibodies that specifically bind β-glucan are readily commercially available. See, also, U.S. Pat. No. 7,893,219 to Cassone et al. (Feb. 22, 2011), the contents of which are incorporated herein by this reference.

LTA, LPS, and β-glucan are cell wall components of gram-positive bacteria, gram-negative bacteria, and fungi, respectively. The presence of such cell wall component(s) in the patient's peritoneal dialysis effluent is indicative both that infection is occurring and the specific type of causative agent(s).

In certain embodiments, other specific antigens can be detected to indicate the presence of the specific pathogen (e.g., bacteria) species in the peritoneal dialysis effluent. Commonly, such specific pathogens are selected from the group consisting of *Staphylococcus aureus, Pseudomonas* spec., *Staphylococcus epidermidis, Staphylococcus haemolyticus*, vancomycin-resistant enterococci, *Candida* sp., *Escherichia coli*, and mixtures thereof.

For example, lysostaphin could be used to detect *Staphylococcus aureus* and exotoxin A could be used to detect *Pseudomonas* spec. Monoclonal and polyclonal anti-lysostaphin antibodies are commercially available from Antibody Research Corporation (St. Peters, Mo., US) under the SKUs 111145 and 111135, respectively. Polyclonal anti-*Pseudomonas* Exotoxin A antibodies produced in rabbit are available from Sigma-Aldrich/Millipore SiGMa under the MDL number MFCD00162779. Similarly, *Staph. aureus*-specific peptidoglycan can be used to specifically detect *Staph. aureus* in PDE. Monoclonal antibodies are available from QED Biosciences, Inc. (San Diego, Calif., US) under the Catalog Nos. 15702, 15703, and 15704; from Meridian Life Science, Inc. (Memphis, Tenn., US) under the Catalog No. C55570M, and from Abcam, Inc. (Cambridge, Mass., US) under the Product name ab37644. These antibodies recognize peptidoglycan of *Staph. aureus*, Protein A-negative *Staph. aureus*, and *Staph. epidermidis*.

Treatment Regimens:

Single agent antibiotics for treating peritonitis include ertapenem (INVANZ™), cefoxitin, doripenem (DORIBAX™), imipenem/cilastatin (PRIMAXIN™), ertapenem, imipenem/cilastatin, meropenem (MERREM™), moxifloxacin (AVELOX™), piperacillin/tazobactam (ZOSYN™), ticarcillin/clavulanate, piperacillin/tazobactam, ticarcillin/clavulanate (TIMENTIN™), and tigecycline (TYGACIL™).

Combination therapy antibiotics include cefepime (MAXIPIME™), cefotaxime (CLAFORAN™), ceftazidime (FORTAZ™), or ceftriaxone (ROCEPHIN™), together with metronidazole (FLAGYL™). Or cefazolin, cefotaxime, ceftriaxone, ciprofloxacin (CIPRO™), levofloxacin (LEVAQUIN™), together with metronidazole. Or cefepime, ceftazidime, ciprofloxacin, levofloxacin, together with metronidazole. Or gentamicin or tobramycin together with clindamycin (CLEOCIN™) or metronidazole (with or without ampicillin). Such antibiotics are typically administered per established protocols.

In treating peritonitis, regimens of imipenem, piperacillin/tazobactam, and a combination of aminoglycosides and metronidazole are often effective.

Antibiotic treatment against *Pseudomonas* sp. typically involves administration of one or more of the following antibiotics: ceftazidime, ciprofloxacin or levofloxacin, gentamicin, cefepime, aztreonam, carbapenems, ticarcillin, and/or ureido penicillins.

Penicillinase-resistant penicillins (flucloxacillin, dicloxacillin) are antibiotics for treating serious methicillin-susceptible *S. aureus* ("MSSA") infections, but first generation cephalosporins (cefazolin, cephalothin and cephalexin), clindamycin, lincomycin and erythromycin are used in less serious MSSA infections or in patients with penicillin hypersensitivity. All serious MRSA infections should be treated with parenteral vancomycin or teicoplanin. Nosocomial strains of MRSA are typically multi-resistant ("mrMRSA"); mrMRSA strains may be treated with a combination of two oral antimicrobials, such as rifampicin and fusidic acid. Lincosamides (clindamycin, lincomycin) or cotrimoxazole may be used to treat less serious MRSA infections. Antibiotics such as linezolid and quinupristin/dalfopristin have anti-staphylococcal activity.

Lateral Flow Devices:

A lateral flow assay ("LFA") (also known as a lateral flow test ("LFT"), lateral flow device ("LFD"), lateral flow immunoassay ("LFIA"), lateral flow immunochromatographic assays, "Dipstick," Pen-side test, Quick/Rapid test, or test strip) is a simple to use diagnostic device to confirm the presence or absence of target analytes, such as pathogens or biomarkers in humans or animals.

Lateral flow assays typically have a control line to confirm that the test is working properly, along with one or more target or test lines. They are designed to incorporate intuitive user protocols and require minimal training to operate. They can be qualitative and read visually, or quantitative when combined with reader technology, such as ADxLR5®.

Lateral flow tests are widely used in human health for point-of-care testing. They can be performed by a healthcare professional or by the patient, and in a range of settings including the laboratory, clinic, or home.

Lateral flow assays can be developed to be used in a dipstick format or in a housed cassette. Both dipsticks and housed tests will work in a similar way, dependent on the industry, sample matrix, and the market requirement.

Although a "competitive assay" could be adapted for use herein (e.g., by utilization of an enrichment method such as centrifugation to increase the sensitivity of detection), sandwich (or "non-competitive") assays are typically preferred for use herein. In a non-competitive immunoassay format, a positive test is typically represented by the presence of a colored line at the test line position. A non-competitive immunoassay format is ideal for large molecular weight analytes with multiple antigenic sites. Generally, non-competitive immunoassays have a lower limit of detection (heightened analytical sensitivity) compared to a competitive format. Typically, non-competitive immunoassays can detect on the order of picograms/mL (parts per trillion) in comparison to nanograms/mL (parts per billion) for the competitive assay format.

Lateral flow devices typically utilize immunoassay technology with a nitrocellulose membrane, colored latex nanoparticles (or labels such as magnetic beads or colored styrene balls), and antibodies, for quick analysis (see, e.g., FIG. 1).

When a sample from a peritoneal dialysis effluent is added to the lateral flow device, the sample flows along the test device passing through a conjugate pad into a nitrocellulose membrane and then onto an absorbent pad to absorb excess sample.

The sample pad acts as the first stage of the absorption process, and in some cases contains a filter to ensure the accurate and controlled flow of the sample. The conjugate pad, which stores the conjugated labels and antibodies, receives the sample. If the target is present, the immobilized conjugated antibodies and labels bind to the target and continue to migrate along the test.

As the sample moves along the device, the binding reagents situated on the nitrocellulose membrane bind to the target at the test line. A colored line forms and the density of the line varies depending on the quantity of the target present. Some targets may require quantification to determine the target concentration such as by using a reader.

Multiplexed lateral flow assays, related methods, and devices are disclosed in U.S. 20050250141A1 to Lambert et al., (Nov. 10, 2005), the contents of which are incorporated herein by this reference, which assays are capable of simultaneously detecting multiple analytes. See also U.S. Pat. No. 6,924,153 B1 to Boehringer et al. (Aug. 2, 2005), U.S. Pat. No. 8,128,871 B2 to Petruno et al. (Mar. 6, 2012), and U.S. Pat. No. 7,785,899 B2 to Saul et al. (Feb. 18, 2005), the contents of each of which are incorporated herein by this reference, for various lateral flow test kits capable of detecting multiple analytes.

Conjugate labels used with lateral flow devices include: colloidal gold, cellulose nanobeads, fluorescent latex, paramagnetic particles, up-converting phosphors, and various fluorescent labels.

In certain embodiments, the cell wall components are detected by dry chemistry if, for example, the specificity of the antibodies in the lateral flow test is inadequate. Dry chemistry is based upon specific recognition of cell wall component(s) by, e.g., enzymes.

Alternatively, a more sophisticated system can be used to acquire quantitative data instead of qualitative data. For example, the immunofluorescence technology together with a reader may be utilized to measure the quantity of markers in peritoneal dialysis effluent to provide more information to the patients and clinicians by comparing the obtained values with a predetermined cutoff value.

The detection of each biomarker or cell wall component is preferably carried out in an individual channel, although all detections are made simultaneously by using the same peritoneal dialysis effluent sample. Such a design can prevent cross-reaction between biomarkers or cell wall component(s).

It is preferred to add peritoneal dialysis effluent sample to each channel. But alternatively, more than one channel can be connected to each other to avoid repeatedly adding the peritoneal dialysis effluent sample. Accordingly, described is a point-of-care device and assay for testing for peritonitis in dialysis effluent, especially in peritoneal dialysis effluent, providing several advantages over conventional assays and improving peritonitis management. The device and methods are inexpensive, rapid, and easy to use by a patient or clinician with only limited training. Also described is a device and method for such testing that will rapidly allow identification of specific microbial agents of peritonitis or other infection, decreasing the time needed to confirm a peritonitis diagnosis, to facilitate early determinations of an optimal treatment regimen (e.g., specific antibiotic therapy or mixed therapy), with the possibility to replace culture testing and hospital-based laboratories altogether, where both sensitivity and specificity of testing are equivalent to laboratory methods.

A particular advantage is that the disclosed device and assay combines both inflammatory marker testing and specific infection agent testing in a single, inexpensive, and simple to use device. The device and assay gives the patient and clinician substantially more information about actual infection and appropriate peritonitis management than previous technology. For example, tests looking only at inflammatory status rely exclusively on non-specific markers of infection. Even if the test is positive for one or more inflammatory markers (alone), the clinician does not gain significant information about which specific type of therapy (e.g., specific type of antibiotic) to prescribe. The disclosed assay adds an agent-specific test (e.g., Gram status, specific bacterium, fungus, etc.) to the inflammatory marker, greatly increasing reliability of the diagnosis of pathogen-associated peritonitis, while reducing the time needed to implement the most appropriate therapy. Further, PDE samples according to the disclosed assay and device do not necessarily require pre-treatment or any special processing before they are applied to the device, so patients can perform the entire test in their homes immediately. As a result, rather than prescribing, for example, an empiric, broad-spectrum antibiotic in response to a generalized confirmation of peritonitis, the clinician can quickly prescribe a targeted antibiotic that is most suitable for treating a known Gram positive or Gram negative bacterial infection. The combined device is also cheaper and easier to use and interpret than two devices or multiple assays, and results can be read in less than 10 minutes in most cases.

In this way, patients can be treated sooner with a much higher probability of being administered with, for example, the most suitable antibiotic for their infection. In some settings, a patient in a home setting could accordingly test their own PDE, identify a specific positive result and report to their clinician, and be directed to begin a course of targeted treatment immediately. Such therapy could be initiated even where other classical signs of infection (e.g., pain, fever, cloudy effluent) are not yet present. Further, the severity and duration of peritonitis in, for example, PD patients may be reduced, allowing them to stay on PD longer without the need for more invasive forms of dialysis, such as hemodialysis. Also reduced is the use of improper antibiotics (i.e., empiric, broad-spectrum antibiotics where a more targeted therapy is indicated), thus reducing the incidence of antibiotic-resistant bacteria in the population.

In certain embodiments, a picture is taken of the results of the test, which are transmitted to a health care practitioner. In certain embodiments, a mobile telephone "app" is used to analyze the results, and provide the patient with a notation to, for example, "Call your health care provider" or "Peritonitis Confirmed." In certain embodiments, this can further include analysis of a picture of the analyte, using technology as described in International Application No.: PCT/EP2017/000803, published on Jan. 11, 2018, the contents of which are incorporated herein by this reference.

FIGS. 1 through 5 and 7 illustrate various embodiments of a lateral flow device according to the invention. In the depicted cases, the device is configured to detect NGAL, LTA, β-glucan, LPS, and IL-6 in one test.

As depicted in FIG. 1, a volume of analyte (e.g., PDE) is deposited into a well portion of the strip. The PDE flows away from the well (e.g., by capillary action), down the strip, and interacts with a conjugate of appropriate labeled antibodies associated with the strip. Other antibodies having the same specificity as the labeled antibodies are affixed to the strip (at the solid phase). If the appropriate antigen is present in the PDE (e.g., NGAL, LTA, β-glucan, LPS, or IL-6), it will bind with the labeled antibodies and form a sandwich complex at the portion of the strip where the solid phase antibodies are present, and the sandwich complex will be detectable. A control line is further depicted to ensure the POCT is performing properly. Excess reagent passes to the end of the strip.

Figure 2:
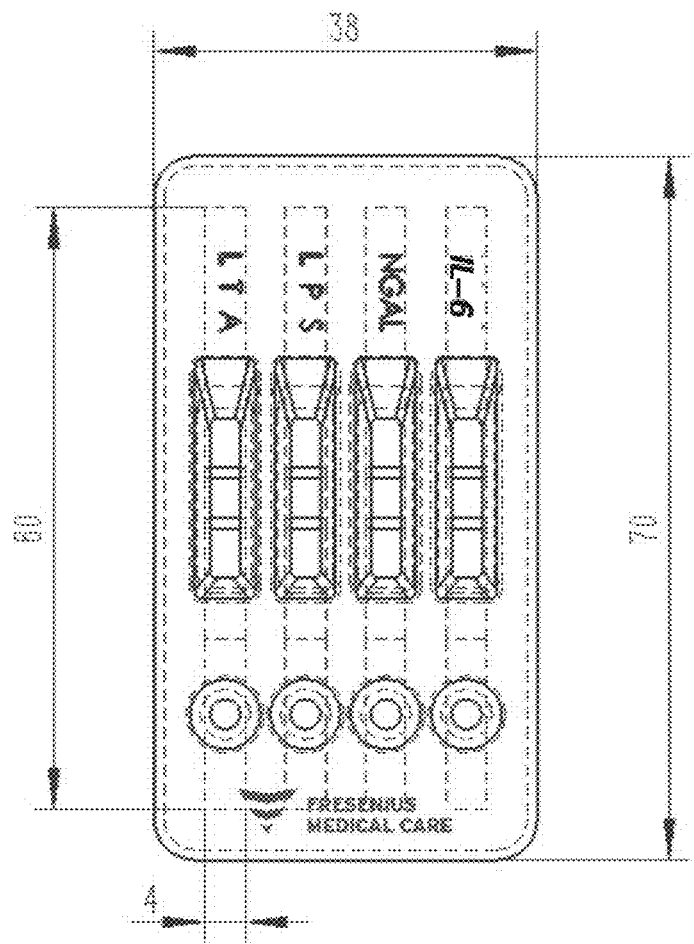
Figure 3:
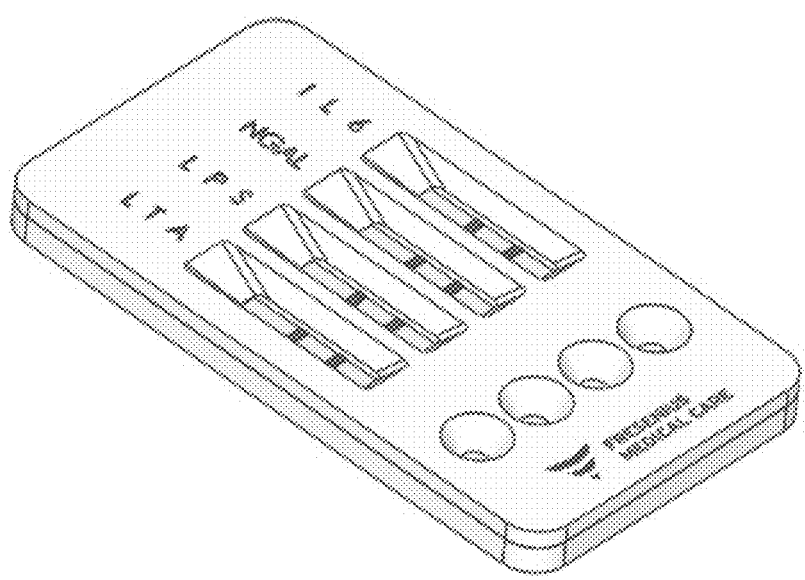

FIGS. 2 and 3 represent various configurations of a lateral flow device according to the disclosure (and FIG. 1), including four sample wells and four roughly-parallel and adjacent channels configured to detect LTA, LPS, NGAL, and IL-6. This embodiment has the advantage of taking up relatively little space, while requiring application of four relatively low-volume PDE samples to utilize all four channels. In FIGS. 2 and 3, the control lines are distal from the wells and test lines closer to the wells.

Figure 4:
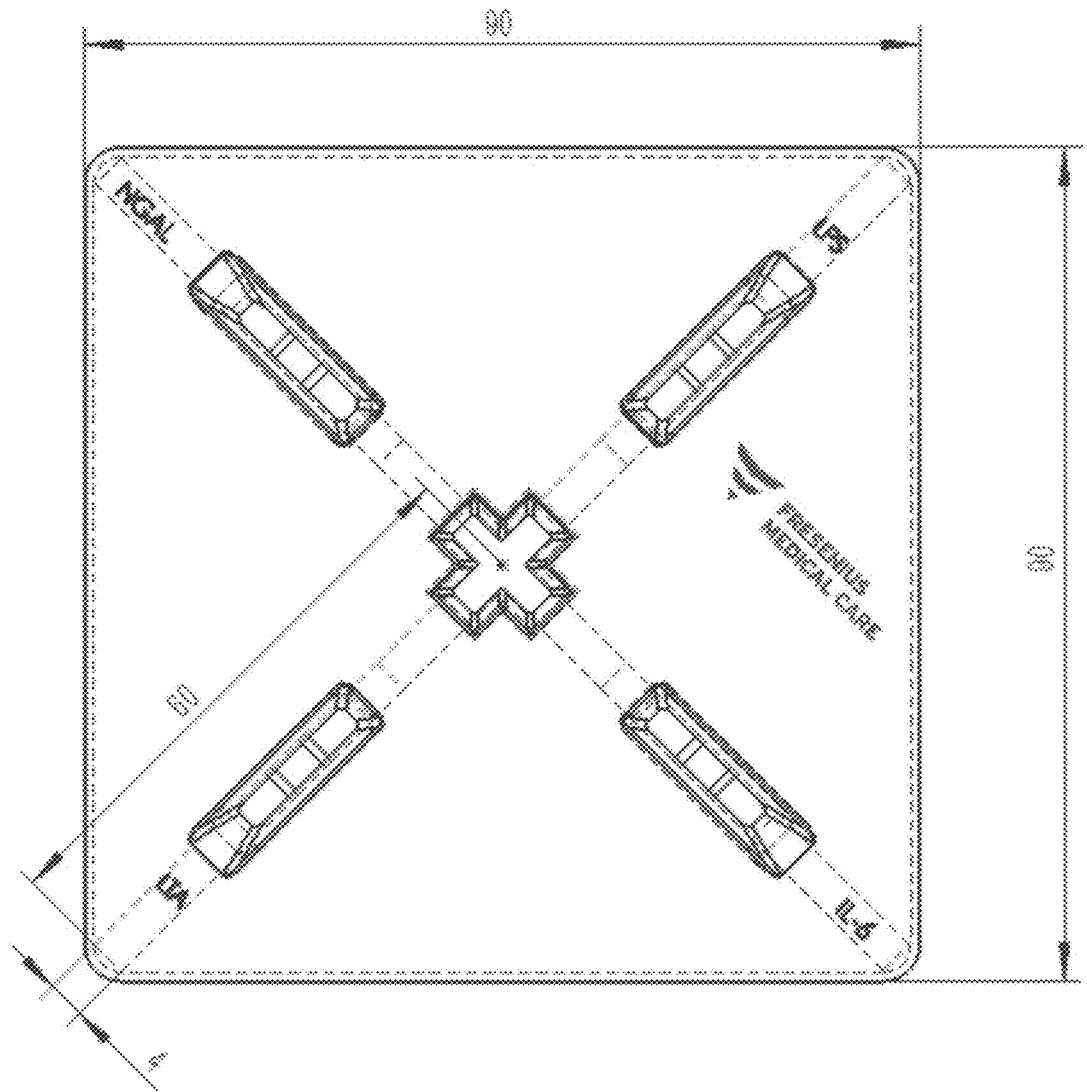
Figure 5:
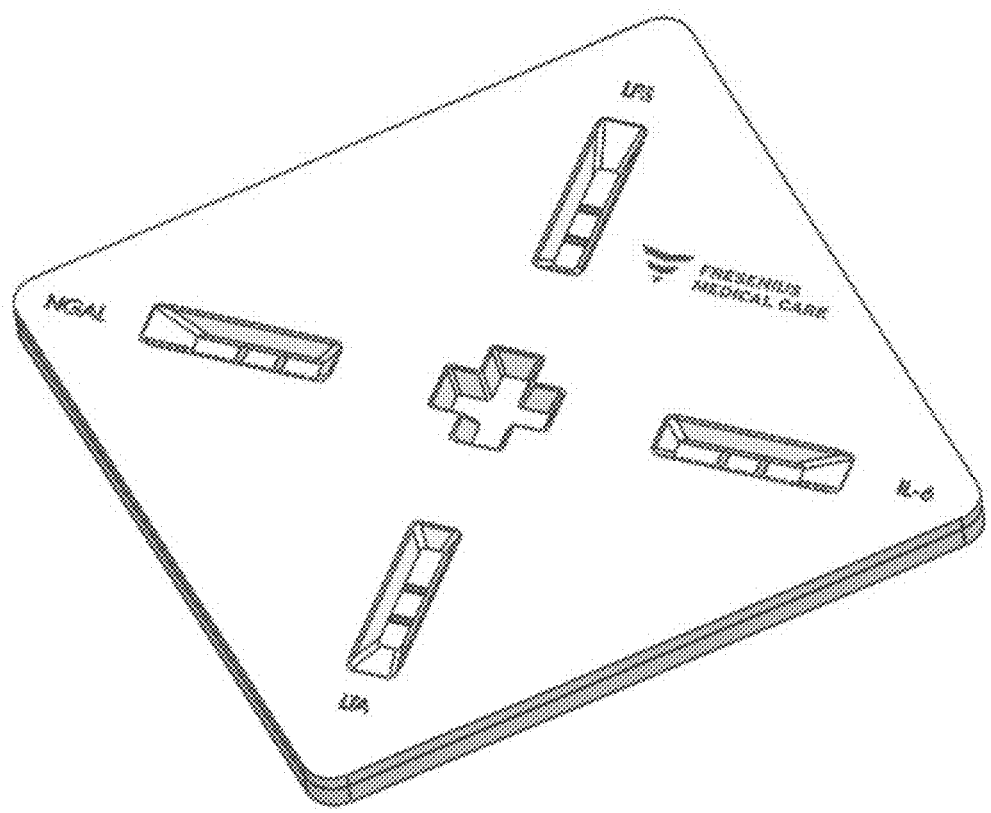

FIGS. 4 and 5 represent an alternative configuration of a lateral flow device of the disclosure, including a single, central sample well and four channels that radiate away from the central well, configured again to detect LTA, LPS, NGAL, and IL-6. This embodiment has the advantage of requiring only one sample of PDE to be applied by the patient or clinician.

FIGS. 2 and 4 also indicate possible dimensions (in millimeters) for the lateral flow device and ranges for such dimensions, according to certain embodiments. For example, the device depicted in FIG. 2 can have a width 38 with a Range of 30~60 mm and a Tolerance of −1~+1, a height 70 having a Range of 55~100 mm and a Tolerance of −1~+1, depicted distance 60 having a Range of 50~80 mm and a Tolerance of −1~+1, and depicted width 4 of the channel having a Range of 2.5~8 mm and a Tolerance of −1~+1. The device depicted in FIG. 4 can have, e.g., a height and width 90 with a Range of 70~120 mm and a Tolerance of −1~+1, depicted distance 60 having a Range of 50~80 mm and a Tolerance of −1~+1, and depicted width of the channel having a Range of 2.5~8 mm and a Tolerance of −1~+1.

Figure 7:
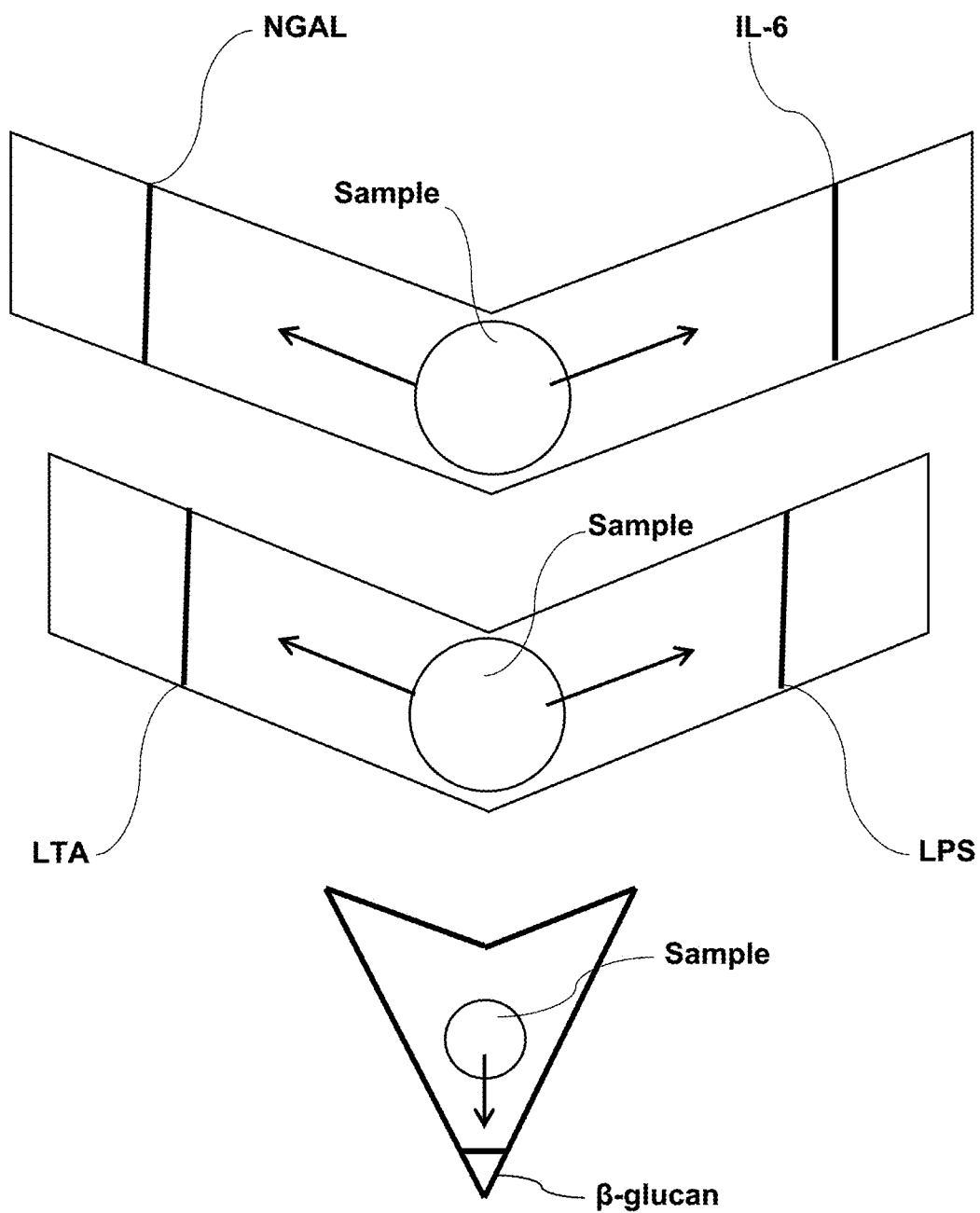

FIG. 7 illustrates a triple-chevron configuration (e.g., FRESENIUS™ logo), to which sample is applied to the center of each chevron. The sample then flows laterally or longitudinally along multiple channels to test lines where appropriate and binding reagents bind antigens that may be present in the samples.

It is preferred to read the results of all analytes at the same time point, for instance, after 15-30 minutes. Alternatively, the results can be read consecutively.

The described samples are peritoneal dialysis effluents. In an embodiment, the peritoneal dialysis effluent is used directly after draining to detect one or more markers of infection. In a preferred embodiment, the peritoneal dialysis effluent is first concentrated and/or filtered, and subsequently used to detect one or more markers of infection.

The shape of the device has no limit so long as the individual channels are maintained.

Although a lateral flow immunoassay is preferred, other techniques such as quantitative immunofluorescence, dry chemistry, etc. can be adapted for use herein.

Methods: In certain embodiments, after a patient has presented in the clinic with a cloudy peritoneal dialysis effluent and/or other symptoms of infection, the practitioner can quickly use the device before sending samples for WBC count and culture. The practitioner can then interpret the results and provide to the nephrologist or supervisor the test results, symptoms, history, etc., along with a possible antibiotics prescription(s).

Alternatively, the device can be used at home by patients. The patient should inform the clinician(s) of the results immediately and follow the suggested instructions for treatment, e.g., orally taken antibiotics, or adding antibiotics directly into fresh dialysis solution for the next exchange. This may happen, for example, outside of clinic hours or for those patients who live in a rural area, without having to wait to present at clinic before implementing a necessary therapeutic regimen.

Alternatively, the device can be used by clinician(s) or the patient to determine whether the prescribed treatment has been effective.

In embodiments, the device is utilized as part of an integrated care management protocol. In certain embodiments, results determined by the device are processed by one or more portable electronic devices (e.g., smartphone app, computer, tablet, etc.) and may be associated with a digital application. The results may in turn be integrated via a cloud or network-based communication path to a remote clinician, laboratory, or other health professional for further evaluation and instruction. Such a remote professional may then direct appropriate clinical action by the patient or on-site professional, such as directing immediate administration of an appropriate antibiotic or other therapy, direct the patient to come to the clinic, or otherwise indicate appropriate care. In some embodiments, a remote professional can send an electronic code to open a medicine lockbox, for example, in the patient's home, with the appropriate medication.

In other embodiments, one or more clinical protocols (i.e., "decision trees") utilizing the described device and/or method are disclosed. Such protocols may be a "test results driven approach" (FIG. 8) as, for example, initiated in response to an observable indicator of infection such as turbidity, or may be "symptom driven" (FIG. 9) as for example may be initiated by a patient symptom such as pain or fever.

Figure 8:
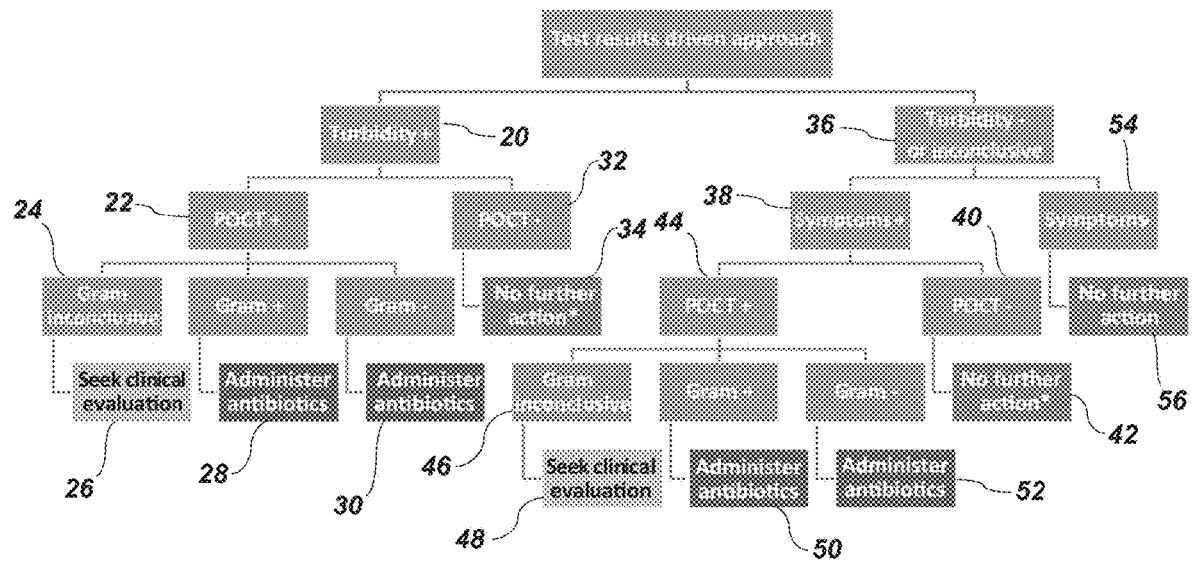
FIG. 8 is a flow diagram of a "test results driven approach."

The "Test results driven approach" of FIG. 8 is applicable to scenarios when turbidity is captured automatically on each treatment, or when the patient undergoes a turbidity test manually after his or her dialysis treatment. As depicted in FIG. 8, if Turbidity is positive ("Turbidity+" 20), then a Point of Care Test ("POCT") as described herein is administered.

If the POCT is positive ("POCT+" 22), then the results of the POCT are analyzed in an attempt to determine the etiology of the infection and appropriate follow up administered. For example, if the etiology of the infection is inconclusive 24, then the patient is requested to seek clinical evaluation 26. If the etiology of the infection is determined to be a Gram+ bacteria ("Gram+"), then an appropriate antibiotic 28 (or other acceptable treatment) is prescribed for the patient. If the etiology of the infection is determined to be a Gram negative bacteria ("Gram–"), then an appropriate antibiotic 30 (or other acceptable treatment) is prescribed for the patient.

If the POCT is negative ("POCT–" 32), then "no further action" 34 may be needed with respect to the patient. However, with respect to this "No further action*" field under the "POCT–" field of the diagram, this assumes, for example, that the point of care test strip's specificity is sufficient to exclude peritonitis (e.g., both bacterial and fungal causes). Thus, in the situation where Turbidity is positive 20, but the POCT is negative 32, the decision tree says "No further action," but it could alternatively be "Seek clinical evaluation" depending on the particular POCT used. For example, if the POCT only identifies bacterial peritonitis, but not other causes of peritonitis (e.g., fungal peritonitis), a patient should still proceed with a clinical evaluation to define the etiology of the turbidity (not shown). A similar situation occurs with the situation Turbidity negative (or inconclusive) 36 with Symptoms positive 38, even if the POCT is negative 40, where the decision tree states "No further action*" 42, a different etiology other than bacterial peritonitis should be considered and a clinical evaluation could be necessary.

In FIG. 8, when Turbidity is negative or inconclusive 36, Symptoms are positive 38, and a POCT is positive 44, the treatment is as before. For example, if the etiology of the infection is inconclusive 46, then the patient is requested to seek clinical evaluation 48. If the etiology of the infection is determined to be a Gram+ bacteria ("Gram+"), then an appropriate antibiotic 50 (or other acceptable treatment) is prescribed for the patient. If the etiology of the infection is determined to be a Gram negative bacteria ("Gram–"), then an appropriate antibiotic 52 (or other acceptable treatment) is prescribed for the patient.

In FIG. 8, if Turbidity is negative or inconclusive 36 and Symptoms are negative 54, then generally, no further action is required 56.

Figure 9:
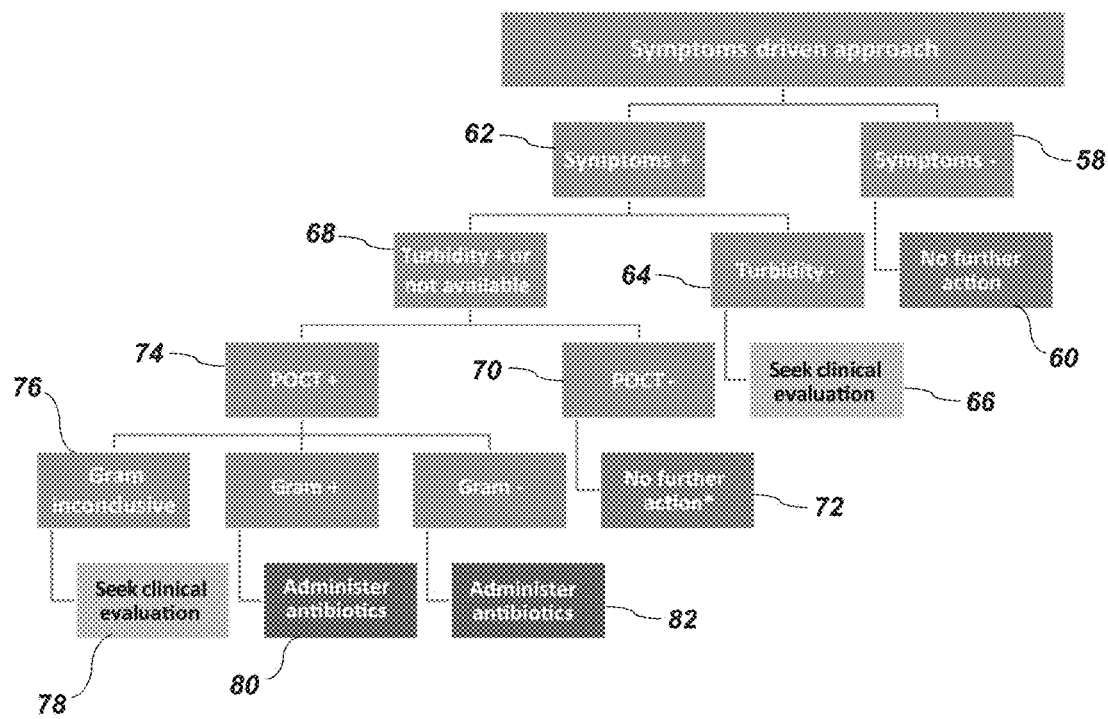
FIG. 9 is a flow diagram of a "symptoms driven approach."

The "symptoms driven approach" of FIG. 9 can be used, for instance, when turbidity is not captured automatically, or when the patient does not undergo a turbidity test after his or her treatment. Under such circumstances, when Symptoms are negative 58, no further action is required 60. However, when Symptoms are positive 62 and a Turbidity test results negative 64, further clinical evaluation 66 is indicated.

When in FIG. 9, Symptoms are positive 62 and a Turbidity test is either positive or not conducted 68, a POCT is preferably conducted.

In FIG. 9, if the POCT is negative 70, no further action 72 may be necessary. Again however, with respect to the "No further action*" field 72 under field "POCT–" 70 of the decision tree, this assumes that the POCT strip(s)'s specificity is sufficient to exclude all etiologies for peritonitis. As with the test results driven approach of FIG. 8, in the "Symptoms driven approach" decision tree of FIG. 9, in the situation Symptoms positive 62 with Turbidity positive (or unavailable) and the POCT negative 72, the recommendation rather than "No further action" would be to "Seek clinical evaluation" (not shown) to rule out, for instance, a fungal etiology.

In FIG. 9, when Turbidity is positive or unavailable 68 and a POCT is positive 74, the treatment is as the Test results driven approach. For example, if the etiology of the infection is inconclusive 76, then the patient is requested to seek clinical evaluation 78. If the etiology of the infection is determined to be a Gram+ bacteria ("Gram+"), then an appropriate antibiotic 80 (or other acceptable treatment) is prescribed for the patient. If the etiology of the infection is determined to be a Gram negative bacteria ("Gram−"), then an appropriate antibiotic 82 (or other acceptable treatment) is prescribed for the patient.

Also, in the Symptoms driven approach, with Symptoms positive and Turbidity negative, one could still beneficially utilize the POCT to benefit the patient (not shown). If the POCT results positive, the same follow up treatments can be used. If the POCT is negative, use "Seek clinical evaluation."

In alternative embodiments of the decision trees, turbidity may be eliminated entirely as a required test, and the decision to implement POCT testing may be driven entirely by the presence or absence of symptoms. This may be the case where, for example, turbidity data is inconclusive or unreliable, or where the clinician or patient wants to expedite the POCT testing, as may be the case where the patient has a history of a specific type or types of peritonitis infections and the primary interest is in narrowing the most likely cause of infection quickly.

In the various approaches, if the POCT is configured to detect the presence of, e.g., a fungal infection (not shown), and this tests positive, then an appropriate antifungal agent and/or therapy may be prescribed.

An advantage of such protocols is that they can be performed remotely, as by a patient in the home or at a remote clinic, and they can exploit the point of care testing device to rapidly identify a causative agent of infection and rapidly institute suitable treatment (e.g., specific antibiotics). In other cases, these protocols can be performed in a clinic with little additional training required of the practitioner, but nevertheless reducing time to appropriate treatment over conventional protocols.

The invention is further described with the aid of the following illustrative Examples.

EXAMPLE I

The assay of FIGS. 1-3 is made with the following antibody components incorporated into a paper-based (e.g., nitrocellulose) LFD:

| Binding Molecule(s) | Supplier | Product No. | Reference |
|---|---|---|---|
| Anti-IL-6 | R&D Systems<br>614 McKinley Place NE<br>Minneapolis, MN 55413 | MAB206 (Capture) | *Cell. Physiol. Biochem.*, 2017; 42(5): 1961-1972 |
| | R&D Systems<br>614 McKinley Place NE<br>Minneapolis, MN 55413 | BAF206 (Detection) | *Cell. Physiol. Biochem.*, 2017; 42(5): 1961-1972 |
| | Abcam<br>1 Kendall Square, Suite B2304<br>Cambridge, MA 02139-1517 | ab48478 (Pair) | |
| Anti-NGAL | R&D Systems<br>614 McKinley Place NE<br>Minneapolis, MN 55413 | MAB17571 (Capture) | |
| | R&D Systems<br>614 McKinley Place NE<br>Minneapolis, MN 55413 | BAF1757 (Detection) | *J. Neurosci.* 2016; 36(20): 5608-22 |
| | Abcam<br>1 Kendall Square, Suite B2304<br>Cambridge, MA 02139-1517 | ab220126 (Pair) | |
| Anti-LPS | Meridian Bioscience<br>3471 River Hills Drive<br>Cincinnati, OH 45244 | C55308M | |
| Anti-LTA | Meridian Bioscience<br>3471 River Hills Drive<br>Cincinnati, OH 45244 | C65380M * | |
| | Meridian Bioscience<br>3471 River Hills Drive<br>Cincinnati, OH 45244 | C65813M * | |
| Anti-*Staph. aureus* (peptidoglycan) | Abcam<br>1 Kendall Square, Suite B2304<br>Cambridge, MA 02139-1517 | ab37644 | |
| | QED Bioscience, Inc.<br>10919 Technology Pl # C,<br>San Diego, CA 92127 | 15704 | |
| | Meridian Life Science, Inc.<br>5171 Wilfong Road<br>Memphis, TN 38134 | C55570M (Detection) | |
| | Invitrogen, Inc.<br>Waltham, MA | MA1-10708, and<br>MA1-10709 (Pair) | |

Antibody list: capture antibody, detector antibody (BSA gold conjugated), anti-biotin gold antibody.

Three drops of PDE sample are placed onto the sample receiving portions of each of the wells of the device shown in FIG. 1, fluid flows into each of the channels and moves by diffusion through the nitrocellulose paper to a capture zone containing a capture (i.e., primary) antibody, and from there continues to a detection zone within a detection window containing one or more detection (i.e., secondary) antibodies. Results are read visually or using an optical reader, mobile device, or similar to determine if the PDE sample is positive for one or more markers of infection and/or inflammation.

EXAMPLE II

Figure 6:
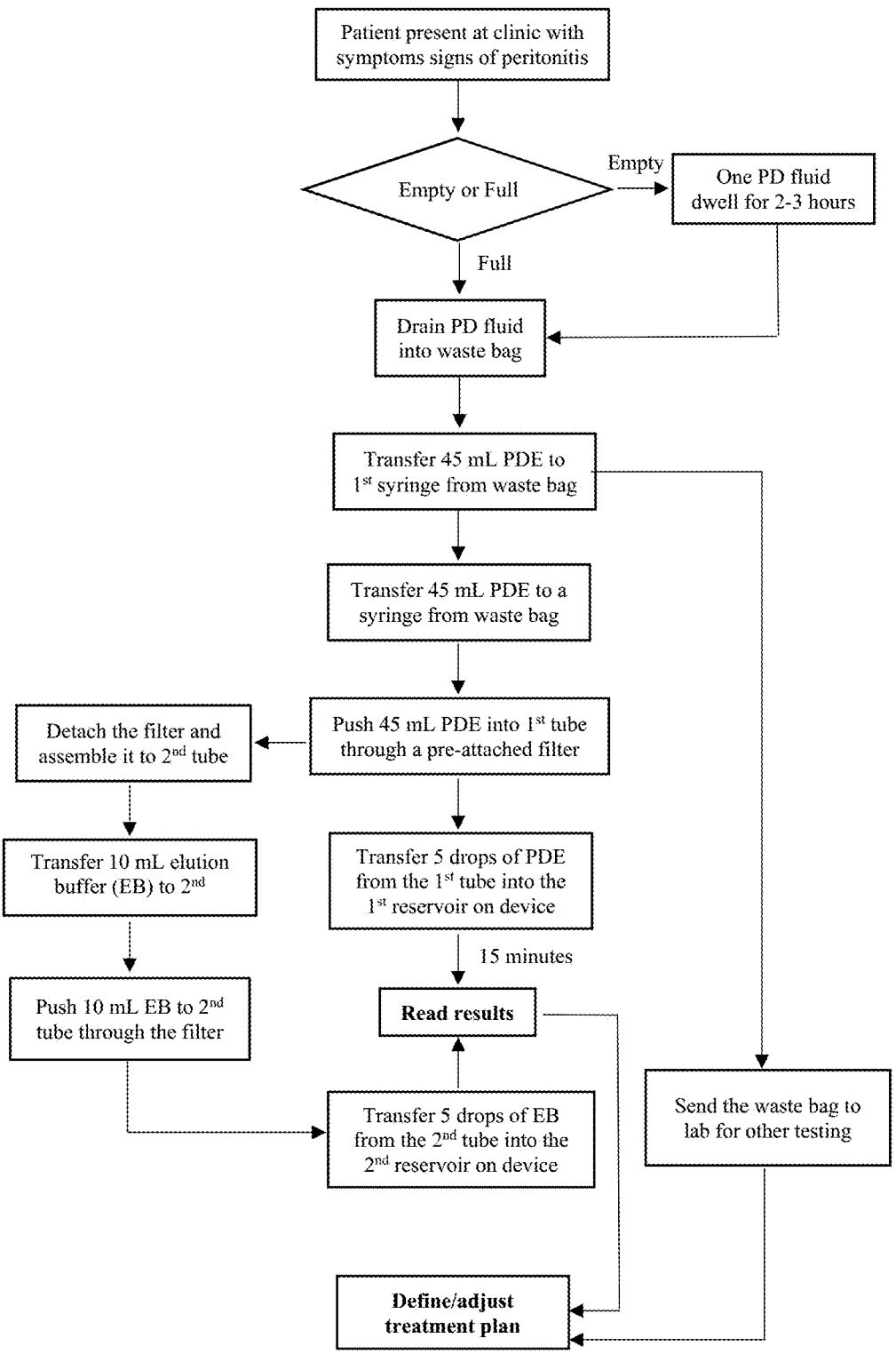
FIG. 6 is a flow diagram of a process according to the disclosure.

Protocol—Rapid PD-related peritonitis diagnosis at dialysis clinic or home (following the flow diagram of FIG. 6).

Background: When a PD patient displays any sign of peritonitis (e.g., cloudy PDE, abdominal pain, and/or fever), he or she is to visit a dialysis clinic or doctor as soon as possible. Upon presentation at the dialysis clinic, the nurse or other health care professional drains the PD effluent into a waste bag and collects samples for routine testing such as cell count, gram stain, and culture. Alternatively, a PD patient may collect and test samples using the disclosed assay and device before going to a dialysis clinic or doctor. What follows is rapid testing of the same PDE sample before it is sent for routine testing (e.g., cell culture, Gram stain, cell count, etc.)
1. Process
   1.1 Equipment and reagents
      1. PPE ("Personal Protective Equipment")
      2. Testing kit contains:
         A sterile 50 mL syringe with a needle pre-attached
         A sterile 10 mL syringe with a needle pre-attached
         Two transparent calibrated droppers
         A sterile 50 mL conical tube with a filter pre-assembled on the top
         A sterile 50 mL conical tube
         A vial with 10 mL elution buffer
         A testing device
   1.2 Procedure
      1. Perform hand hygiene and wear PPE.
      2. Clean work surface with detergent.
      3. Unwrap the testing kit and gather the materials for use.
      4. Follow the clinic's standard operating procedures to drain the PDE into the drain bag and label the bag.
      5. Use a sterile syringe to take 45 mL PDE sample through the injection port on the drain bag.
      6. Discard the needle.
      7. Attach the syringe to a round filter (Ø50 mm) which is pre-assembled with a 50 mL conical tube.
      8. Push the 45 mL PDE sample into the conical tube through the filter.
      9. Take out the testing device and place it on the flat and clean work surface.
      10. Disassemble the filter and assemble it to the other sterile 50 mL conical tube.
      11. Transfer 5 mL of PDE sample that is collected in step 8 and dispense 5 drops (~0.25 mL) into the $1^{st}$ sample reservoir on the testing device of EXAMPLE I.
      12. Wait for 15 minutes to read the results by checking the color of the two lines.
      13. During the waiting time, use the other syringe to collect all the elution buffer in the vial.
      14. Discard the needle.
      15. Attach the syringe to the filter that was assembled to the other conical tube at step 10.
      16. Push the elution buffer into the conical tube through the filter.
      17. Transfer 5 mL of PDE sample that is collected in step 16 and dispense 5 drops (~0.25 mL) into the $2^{nd}$ sample reservoir on the testing device.
      18. Wait for another 10-15 minutes to read the results.

Send the drain bag to lab for other testing.

EXAMPLE III

Enrichment by UF Membrane 25 ml of PDE is placed into a container for centrifugation, which is separated into an upper chamber and a lower chamber by an ultrafiltration ("UF") membrane having a molecular weight cutoff of 29,000. The container is capped and placed into a centrifuge and spun (×4000 g). The PDE is filtered through the UF membrane and pushed from the upper chamber to the lower chamber, creating an enriched PDE.

A few drops of the enriched PDE are placed onto the sample port of the IL-6/NGAL panel of the device of EXAMPLE I, and any reaction is determined.

The UF membrane is mixed with elution buffer, and a few drops are placed onto the sample port of the LPS/LTA panel of the device of EXAMPLE I, and any reaction determined.

EXAMPLE IV

Detection of Inflammatory and Gram status markers in PDE samples

87 PDE samples were recruited, including 9 Peritonitis samples and 78 Non-peritonitis samples. NGAL and IL-6 reference levels for each sample were determined with JiuQiang biochemistry NGAL test and the SIEMENS chemiluminescence IL-6 test.

A device corresponding to FIGS. 2 and 3 was used to analyze the samples. The assay had 4 strips corresponding to NGAL, IL-6, LTA, and LPS. NGAL and IL-6 were used as inflammatory indicators for peritonitis. LTA was used as an indicator of Gram positive bacterial infection. LPS was used as an indicator for Gram negative bacterial infection, with the following reagents associated with each of the relevant strips:

NGAL:
a) Control line: ShangDong ShuoJing Goat-anti-mouse antibody
b) Test line: NanJing GenScript NGAL Antibody (4C10A7)
c) Conjugate: NanJing GenScript NGAL Antibody (5A9D12)
d) Nitrocellulose membrane: Millipore HF13502S18
e) The limit of detection of the NGAL test was optimized at 80 ng/ml.

IL-6
a) Control line: ShangDong ShuoJing Goat-anti-mouse antibody
b) Test line: Novoprotein (DA012)
c) Conjugate: Novoprotein (DA011)

d) Nitrocellulose membrane: Millipore HF13502S18
e) The limit of detection of IL-6 test was optimized to be 200 pg/ml & 300 pg/ml LTA
a) Control line: ShangDong ShuoJing Goat-anti-mouse antibody
b) Test line: Streptavidin Hangzhou KuaiGe technology (20190307-1)
c) Conjugate: Biorbyt (orb23891)
d) Biotinylation: Biorbyt (orb23822)
e) Nitrocellulose membrane: Millipore HF13502S18

LPS
a) Control line: HangZhou LongJi biotech (lot 181114)
b) Test line: Thermo Fisher PA1-73178
c) Conjugate: Thermo Fisher PA1-28903
d) Nitrocellulose membrane: Millipore HF13502S18

Test results were visually read, with a negative result indicated if the control line was positive and test line was negative; and a positive result indicated if the control line and test line were positive. See FIGS. 1-3.

All 87 PDE samples were tested with the device of FIG. 1 for the NGAL test and IL-6 test. 78 non-peritonitis samples were tested for LTA and LPS. The following Tables show the results.

TABLE A

Specificity for NGAL, IL-6, LTA, and LPS in Peritoneal Dialysis Effluents

|  | NGAL | IL-6 200 | NGAL + IL-6 200 | LTA | LPS |
| --- | --- | --- | --- | --- | --- |
| Testing number | 78 | 78 | 78 | 78 | 18 |
| Negative result | 56 | 66 | 70 | 75 | 18 |
| Specificity | 56/78 | 66/78 | 70/78 | 75/78 | 18/18 |
|  | 71.8% | 84.6% | 89.7% | 96.6% | 100% |

TABLE B

Sensitivity for NGAL and IL-6 in PDE

|  | NGAL | IL-6 200 | NGAL/IL-6 200 |
| --- | --- | --- | --- |
| Testing number | 9 | 9 | 9 |
| Positive result | 9 | 9 | 9 |
| Sensitivity | 9/9 | 9/9 | 9/9 |
|  | 100.0% | 100.0% | 100.0% |

As can be seen, the combination of the NGAL 80 ng/ml & IL-6 200 pg/ml combination indicator presents the best sensitivity and specificity for these markers in peritonitis detection. In the same experiments, the specificity for LTA was 96.6% and for LPS was 100%.

The sensitivity for LTA and LPS in the described PDE samples was separately tested using spiked bacterial peritoneal dialysis samples and negative peritoneal dialysis samples for comparison. Three Gram positive bacterial species commonly associated with peritonitis were used: *Staphylococcus aureus* (CMCC(B) 26001), *Staphylococcus epidermidis* (ATCC 12228), and beta hemolytic *Streptococcus* (CMCC(B) 32210). Two Gram negative bacteria commonly associated with peritonitis were selected: *E. coli* 0157:H7 (ATCC35150) and *Pseudomonas aeruginosa* (ATCC 27853). Bacteria were cultured on plate media. After they were enriched, the colony was moved to phosphate buffer from the plate media. Bacteria concentration was determined using McIntosh turbidity. Each concentrated bacteria solution was spiked to 10 individual PDEs. For *Staphylococcus aureus*, *Staphylococcus epidermidis* and Beta hemolytic *Streptococcus*, the bacteria was diluted to $1 \times 10^7$ CFU/ml. *E. coli* O157:H7 was diluted to $5 \times 10^6$ CFU/ml. *P. aeruginosa* was diluted to $1 \times 10^9$ CFU/ml. A total of 50 spiked peritonitis samples were generated. 30 PDEs were "spiked" with Gram positive bacteria. 20 PDEs were spiked with Gram negative bacteria. Each sample was tested with an LTA test and LPS test. The testing results were summarized in the following table:

TABLE C

Limit of Detection for LTA and LPS in Gram Positive and Gram Negative Bacteria Spiked PD Samples

| | | | LTA | | LPS | |
| --- | --- | --- | --- | --- | --- | --- |
| Gram | Bacteria | CFU/ml | Negative | Positive | Negative | Positive |
| Positive | S. aureus | $1*10^7$ | 0/10 | 10/10 | 10/10 | 0/10 |
| | S. epidermidis | $1*10^7$ | 0/10 | 10/10 | 10/10 | 0/10 |
| | streptococcus | $1*10^7$ | 0/10 | 10/10 | 10/10 | 0/10 |
| Negative | E. coli O157:H7 | $5*10^6$ | 10/10 | 0/10 | 0/10 | 10/10 |
| | P. aeruginosa | $1*10^9$ | 10/10 | 0/10 | 0/10 | 10/10 |

The sensitivity of LTA for Gram positive bacteria was 30/30=100%. The sensitivity of LPS for Gram negative bacteria was 20/20=100%. No cross reaction was found between Gram positive strains and the LPS test, or between Gram negative strains and the LTA test.

EXAMPLE V

An additional 19 non-peritonitis PDE samples were recruited and tested for NGAL, IL-6, LTA, and LPS specificity as described in Example IV, using Magpix for quantitation of NGAL and IL-6. Table D shows the results:

TABLE D

Specificity for NGAL, IL-6, LTA, and LPS in Peritoneal Dialysis Effluents

|  | NGAL | IL-6 200 | NGAL/IL-6 200 | LTA | LPS |
| --- | --- | --- | --- | --- | --- |
| Testing number | 19 | 19 | 19 | 19 | 19 |
| Negative result | 18 | 19 | 19 | 19 | 19 |
| Specificity | 18/19 | 19/19 | 19/19 | 19/19 | 19/19 |
|  | 94.7% | 100.0% | 100.0% | 100.0% | 100.0% |

The combination of NGAL 80 ng/ml & IL-6 200 pg/ml presents 100% specificity with 19 PDEs from normal patients. LTA and LPS tests also presents 100% specificity with the 19 PDEs.

EXAMPLE VI

Combined Sensitivity and Specificity

The results of Example V and Example IV were compiled to derive a composite sensitivity and specificity as shown in Tables E, F, and G.

TABLE E

Combined Specificity

|  | NGAL | IL-6 200 | NGAL/ IL-6 200 | LTA | LPS |
|---|---|---|---|---|---|
| Testing number | 97 | 97 | 97 | 97 | 37 |
| Negative result | 74 | 85 | 89 | 94 | 37 |
| Specificity | 74/97 | 85/97 | 89/97 | 94/97 | 37/37 |
|  | 76.3% | 87.6% | 91.8% | 96.9% | 100.0% |

TABLE F

Combined Sensitivity

|  | NGAL | IL-6 200 | NGAL/IL-6 200 |
|---|---|---|---|
| Testing number | 9 | 9 | 9 |
| Positive result | 9 | 9 | 9 |
| Sensitivity | 9/9 | 9/9 | 9/9 |
|  | 100.0% | 100.0% | 100.0% |

TABLE G

Total Agreement for Both Positive and Negative PDE Samples

|  | NGAL | IL-6 200 | NGAL/IL-6 200 |
|---|---|---|---|
| Testing number | 106 | 106 | 106 |
| Agreement number | 83 | 94 | 98 |
| Total | 83/106 | 94/106 | 98/106 |
| Agreement | 78.3% | 88.7% | 92.5% |

The assay showed a good ability to detect peritonitis in PDE samples, with specificity of 91.8% and sensitivity of 100%. The assay also indicated the specific type of pathogen of infection. The most frequent bacterial pathogens associated with peritonitis can be detected and distinguished as Gram negative or Gram positive.

EXAMPLE VII

Specific Detection and Treatment

The assay/assay kit as described above (e.g., such as shown in FIGS. 1 through 5) is modified to include a binding molecule that specifically binds to an antigen indicative of the presence of a specific pathogen species, in this example, Staphylococcus aureus by substituting antibodies specific for S. aureus (e.g., ab37644 from Abcam, catalog number 15704 from QED Bioscience, Inc., or C55570M from Meridian Life Science, Inc.) for one of the antibodies used in the standard assay (i.e., specific for LTA, LPS, NGAL, IL-6, or β-glucan). When a subject is determined to be suffering from peritonitis caused by S. aureus, the subject is administered appropriate antibiotic therapy (e.g., cotrimoxazole) to treat the peritonitis in view of the diagnosis.

EXAMPLE VIII

The assay/assay kit as described in FIGS. 1 and 2 [having four parallel lanes] was modified to include an antibody that specifically binds to the peptidoglycan antigen of Staphylococcus aureus (MA1-10708 and MA1-10709 from Invitrogen, Inc.), instead of the LTA-specific antibody. "Non-peritonitis" PDE samples (PDE 83-88) (n=6), PDE samples spiked with varying concentrations of S. aureus (n=6), and a peritonitis-positive PDE sample known to be culture positive for S. aureus (n=1) were analyzed using the modified assay as described. The results are shown in the Table below.

TABLE D

S. aureus specific analysis

| Non-peritonitis | | PDE 83 | Negative |
|---|---|---|---|
|  |  | PDE 84 | Negative |
|  |  | PDE 85 | Negative |
|  |  | PDE 86 | Negative |
|  |  | PDE 87 | Negative |
|  |  | PDE 88 | Negative |
| Staphylococcus aureus | | 5*10^4 CFU/ml | Negative |
|  |  | 1*10^5 CFU/ml | Negative |
|  |  | 1*10^6 CFU/ml | Positive |
|  |  | 1*10^7 CFU/ml | Positive |
|  |  | 1*10^8 CFU/ml | Positive |
|  |  | 1*10^9 CFU/ml | Positive |
| Peritonitis (culture positive with S. aureus) | | PDE 80 | Positive |

As can be seen, all "non-peritonitis" samples tested negative for S. aureus (100% specificity). Peptidoglycan specific to S. aureus was detected in the spiked samples, with a limit of detection of 1×106 CFU/ml, as well as in the S aureus culture positive PDE sample.

EXAMPLE IX

As illustrated in FIG. 8, the decision tree/protocol is initiated by a turbidity test, which can be patient/practitioner initiated (as using a visual inspection or cell-phone based scan of the dialysis bag) or can be monitored using one or more sensors integrated with the dialysis bag or tubing. Examples of turbidity methods that may be suitable for use in the present disclosure may be found in PCT Publication WO2018/007013, filed Jul. 7, 2017 and titled "Method and Smartphone for Detecting Symptoms of Peritonitis," the contents of which are incorporated herein by this reference. This decision tree can be initiated even in the absence of symptoms, permitting a possibly earlier detection of infection than is customarily seen in current practice. If turbidity is positive 20, samples of the PD effluent are applied to the disclosed device to evaluate Gram status. Appropriate antibiotic therapy can be rapidly initiated based on a Gram+ or Gram− result, or the patient can be directed to further evaluation by a clinician if Gram status is inconclusive. If the POCT test is negative 32 with a positive turbidity test, the patient can be directed to take no further action (assuming symptoms are absent) or to seek further clinical evaluation 34 (e.g., depending on the breadth of the POCT in detecting, for instance, fungal infections).

In similar fashion for this decision tree, if turbidity is negative or inconclusive 36, then the presence of symptoms 38 will determine whether the POCT device should be deployed.

EXAMPLE X

Symptom-Driven Patient Decision Tree

As illustrated in FIG. 9, this decision tree is primarily symptom-driven and may be utilized for example in situations where turbidity is not captured automatically or where patients are not routinely performing turbidity tests after treatment.

In this approach, the presence of one or more symptoms 62 of infection would indicate that a turbidity test be taken. If turbidity is positive or not available 68, the patient would then be directed to use the POCT device. If the POCT device reports either a Gram+ or Gram− bacterium is present, appropriate antibiotic therapy 80, 82 can be immediately implemented. Where symptoms are present 62, but turbidity is absent 64, the patient may be directed to clinical evaluation 66. One advantage of this protocol, however, is that a symptomatic patient with turbidity 68 will be able to make a rapid determination of the likely cause of infection (Gram+ or Gram−, or even the specific bacterial, fungal, or other agent), before even presenting to the clinician, allowing a much faster determination of appropriate treatment.

In this approach, where symptoms are absent 58, the patient would be directed to take no further action 60. However, in all cases where the patient is experiencing one or more symptoms 62, the POCT device may recommend the patient to determine if a specific cause of infection is present.

The entire contents of all cited references are specifically incorporated by reference in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed.

Other embodiments of the instant disclosure will be apparent to those skilled in the art from consideration of the present specification and practice of the instant disclosure disclosed herein. It is intended that the present specification and examples be considered as exemplary only with a true scope and spirit of the invention being indicated by the following claims and equivalents thereof.

What is claimed is:

1. An assay kit for analyzing a sample from a subject, the assay kit comprising:
   a binding molecule that specifically binds an antigen indicative of a subject launching an inflammatory response in the peritoneum, wherein the antigen indicative of a subject launching an inflammatory response in the peritoneum is neutrophil gelatinase-associated lipocalin (NGAL);
   a binding molecule that specifically binds an antigen indicative of the presence of Gram-negative bacteria, wherein the antigen indicative of the presence of Gram-negative bacteria is lipopolysaccharide (LPS);
   a binding molecule that specifically binds an antigen indicative of the presence of Gram-positive bacteria, wherein the antigen indicative of the presence of Gram-positive bacteria is lipoteichoic acid (LTA); and
   a binding molecule that specifically binds an antigen indicative of the presence of *Staphylococcus aureus*, wherein the an antigen indicative of the presence of *S. aureus* is peptidoglycan (PGN).

2. The assay kit of claim 1, further comprising:
   a binding molecule that specifically binds an antigen indicative of the presence of a fungus, wherein the antigen indicative of the presence of a fungus is β-glucan.

3. An assay kit for analyzing a sample from a subject, the assay kit comprising:
   a binding molecule that specifically binds an antigen indicative of a subject launching an inflammatory response in the peritoneum, wherein the antigen indicative of a subject launching an inflammatory response in the peritoneum is neutrophil gelatinase-associated lipocalin (NGAL);
   a binding molecule that specifically binds an antigen indicative of the presence of Gram-negative bacteria, wherein the antigen indicative of the presence of Gram-negative bacteria is lipopolysaccharide (LPS);
   a binding molecule that specifically binds an antigen indicative of the presence of Gram-positive bacteria, wherein the antigen indicative of the presence of Gram-positive bacteria is lipoteichoic acid (LTA); and
   a binding molecule that specifically binds an antigen indicative of the presence of a fungus.

4. The assay kit of claim 3, wherein β-glucan is the antigen indicative of the presence of a fungus.

5. The assay kit of claim 3, further comprising:
   a binding molecule that specifically binds an antigen indicative of the presence of a specific pathogen species in a peritoneal dialysis effluent.

6. The assay kit of claim 5, wherein the specific pathogen is selected from the group consisting of *Staphylococcus aureus*, Methicillin-resistant *Staphylococcus aureus*, a Coagulase-negative staphylococcal species *Staphylococcus epidermidis*, *Staphylococcus haemolyticus*, a *Streptococcus* sp., an *Escherichia coli*, a *Candida* sp., an *Aspergillus* sp., and a vancomycin-resistant *Enterococcus* sp.

7. The assay kit of claim 3, further comprising:
   means for filtering, concentrating and/or enriching antigen(s) from peritoneal dialysis effluent.

8. The assay kit of claim 3, further comprising:
   a buffer that elutes antigen(s) from a sample from a subject.

9. A method of diagnosing peritonitis in a peritoneal dialysis patient, the method comprising:
   contacting peritoneal dialysis effluent of the patient with the binding molecules of the assay kit of claim 3 so as to diagnose peritonitis by determining whether the patient is launching an inflammatory response in the peritoneum, whether Gram-negative bacteria are present in the peritoneal dialysis effluent, whether Gram-positive bacteria are present in the peritoneal dialysis effluent, and/or whether fungus is present in the peritoneal dialysis effluent.

10. A method of treating peritonitis in a peritoneal dialysis patient, the method comprising:
    contacting peritoneal dialysis effluent of the patient with the binding molecules of the assay kit of claim 3 so as to diagnose peritonitis by determining whether the patient is launching an inflammatory response in the peritoneum, whether Gram-negative bacteria are present in the peritoneal dialysis effluent, whether Gram-positive bacteria are present in the peritoneal dialysis effluent, and/or whether fungus is present in the peritoneal dialysis effluent, and then
    administering an appropriate antibiotic to the patient to treat the peritonitis in view of the diagnosis.

11. A method of diagnosing peritonitis in a peritoneal dialysis patient, the method comprising:
    contacting peritoneal dialysis effluent of the patient with the binding molecules of the assay kit of claim 3, and using the binding molecule that specifically binds NGAL to detect an antigen indicative of the patient having launched an inflammatory response in the peritoneum that may be present in the peritoneal dialysis effluent;

using the binding molecule that specifically binds LTA to detect in the peritoneal dialysis effluent an antigen indicative of the presence of Gram-positive bacteria that may be present in the peritoneal dialysis effluent;

using the binding molecule that specifically binds LPS to detect in the peritoneal dialysis effluent an antigen indicative of the presence of Gram-negative bacteria that may be present in the peritoneal dialysis effluent, and using the binding molecule that specifically binds an antigen indicative of the presence of a fungus to detect in the peritoneal dialysis effluent an antigen indicative of the presence of a fungus, so as to diagnose peritonitis by determining whether the patient is launching an inflammatory response in the peritoneum, whether Gram-negative bacteria are present in the peritoneal dialysis effluent, whether Gram-positive bacteria are present in the peritoneal dialysis effluent, and/or whether fungus is present in the peritoneal dialysis effluent.

12. The method according to claim 11, wherein β-glucan is the antigen indicative of the presence of a fungus.

13. The method according to claim 11, further comprising:
detecting in the peritoneal dialysis effluent an antigen indicative of the presence of a specific pathogen species in a peritoneal dialysis effluent.

14. The method according to claim 13, wherein the specific pathogen is selected from the group consisting of *Staphylococcus aureus, Staphylococcus epidermidis, Staphylococcus haemolyticus, Escherichia coli*, a *Candida* sp., and a vancomycin-resistant *Enterococcus* sp.

15. The method according to claim 11, further comprising:
filtering, concentrating, and/or enriching the peritoneal dialysis effluent prior to detecting antigen(s).

16. The assay kit of claim 3, further comprising:
a binding molecule that specifically binds peptidoglycan (PGN).

* * * * *